US009907781B2

(12) United States Patent
Mercenier et al.

(10) Patent No.: US 9,907,781 B2
(45) Date of Patent: Mar. 6, 2018

(54) EPICATECHIN FOR ALLEVIATING SYMPTOMS OF ALLERGY

(75) Inventors: Annick Mercenier, Bussigny (CH); Anurag Singh, Ecublens (CH); Sebastien Holvoet, Palezieux Village (CH); Fabiola Dionisi, Epalinges (CH); Lucas Actis Goretta, Lausanne (CH)

(73) Assignee: Nestec S.A., Vevey (CH)

( * ) Notice: Subject to any disclaimer, the term of this patent is extended or adjusted under 35 U.S.C. 154(b) by 320 days.

(21) Appl. No.: 14/240,134

(22) PCT Filed: Aug. 23, 2012

(86) PCT No.: PCT/EP2012/066388
§ 371 (c)(1),
(2), (4) Date: Feb. 21, 2014

(87) PCT Pub. No.: WO2013/026897
PCT Pub. Date: Feb. 28, 2013

(65) Prior Publication Data
US 2014/0193534 A1    Jul. 10, 2014

(30) Foreign Application Priority Data

Aug. 24, 2011  (EP) .................................... 11178620

(51) Int. Cl.
*A61K 31/353* (2006.01)
*A61K 36/82* (2006.01)
*A61K 36/185* (2006.01)
*A61K 36/73* (2006.01)
*A23K 20/111* (2016.01)
*A23K 50/40* (2016.01)
*A23L 33/105* (2016.01)

(52) U.S. Cl.
CPC .......... *A61K 31/353* (2013.01); *A23K 20/111* (2016.05); *A23K 50/40* (2016.05); *A23L 33/105* (2016.08); *A61K 36/185* (2013.01); *A61K 36/73* (2013.01); *A61K 36/82* (2013.01); *A23V 2002/00* (2013.01); *A23V 2200/00* (2013.01); *A23V 2200/304* (2013.01); *A23V 2200/318* (2013.01); *A23V 2250/2116* (2013.01)

(58) Field of Classification Search
None
See application file for complete search history.

(56) References Cited

U.S. PATENT DOCUMENTS 6,855,352 B2 *  2/2005  Shoji ..................... A23L 1/3002
                                                          424/765
8,911,803 B2 * 12/2014  Holvoet ................. A23L 1/296
                                                          424/439
2009/0286869 A1  11/2009  Schmitz

FOREIGN PATENT DOCUMENTS

| CN | 101352431 | 1/2009 |
| GB | 2463080 | 3/2010 |
| JP | 2004075619 | 3/2004 |
| JP | 2006096694 | 4/2006 |
| JP | 2009-060800 | * 3/2009 |
| WO | 2006003750 | 1/2006 |
| WO | 2010124997 | 11/2010 |

OTHER PUBLICATIONS

English translation of JP 2006-096694 (Toshihiko—2006).*
Ling "Antioxidant Food and Health", Chemical Industry Press, 1st Edition, 2004, pp. 163-165.
Chen et al. "New Products and Technologies Regarding Food Additives", Jiangsu Science and Technology Press, 1st Edition, 2002, p. 122.
Lu et al. "Technology for Extraction and Separation of Active Ingredients of Traditional Chinese Medicine" Chemical Industry Press, 2nd Edition, 2008, p. 346.
Kanda et al.; "Inhibitory effects of apple polyphenol on induced histamine release from RBL-2H3 cells and rat mast cells," Bioscience Biotechnology Biochemistry, 1998, vol. 62, pp. 1284-1289. XP002364768.
Kishi et al. "Clinical Efficacy of Apple Polyphenol for Treating Cedar Pollinosis" Bioscience, Biotechnology, and Biochemistry, 2005, vol. 69, No. 4, pp. 829-832.

* cited by examiner

*Primary Examiner* — Susan Hoffman
(74) *Attorney, Agent, or Firm* — K&L Gates LLP

(57) ABSTRACT

The present invention relates to epicatechin for use in the prevention or reduction of symptoms of an allergic disorder and/or an allergic reaction. The invention further relates to epicatechin for said use in the form of food, food product, food supplement or pharmaceutical products.

15 Claims, 3 Drawing Sheets

EPICATECHIN FOR ALLEVIATING SYMPTOMS OF ALLERGY

CROSS REFERENCE TO RELATED APPLICATIONS

The present application is a National Stage of International Application No. PCT/EP2012/066388, filed on Aug. 23, 2012, which claims priority to European Patent Application No. 11178620.8, filed Aug. 24, 2011, the entire contents of which are being incorporated herein by reference.

FIELD OF THE INVENTION

The present invention relates to epicatechin for use in the secondary prevention of an allergic disorder and/or an allergic reaction.

BACKGROUND OF THE INVENTION

The incidence of allergic disorders has increased dramatically in the developed world and a variety of factors (e.g. environment, genetics, hygiene, diet) are known to impact on their development. Allergies may start in predisposed individuals from early infancy, e.g. as atopic eczema, limited to or followed by the development of food allergies. Respiratory allergies such as allergic rhinitis and asthma occur later in life and complete the sequel of allergic manifestations. Allergies correspond to a deregulated immune response to a variety of allergens normally present either in the environment, such as dust mite or pollen, or in food, such as milk, eggs, nuts or wheat. Recent advances in the understanding of the pathophysiology of allergy have revealed a series of complex immune cell interactions that could be manipulated to influence either sensitization to the allergen (i.e. prevention) or help to alleviate allergic manifestations and symptoms.

A majority of therapeutic options available today for allergies such as corticosteroids and anti-histaminics are aimed at treating different allergic symptoms. While proven to be highly effective, numerous factors such as dose, route and scheme of administration account for the efficacy of these treatments, notwithstanding the adverse effects that are sometimes associated with a chronic use of these medications.

Nutritional interventions to prevent the development or to manage the symptoms of allergic diseases are a promising alternative to medications and have been assessed in numerous pre-clinical and clinical settings. Typically, the protective effects of probiotic bacteria (Kalliomaki et al., Lancet. 2001, 357:1076-9), prebiotics (Arslanoglu et al. 2008, J Nutr 138:1091-1095) and poly-unsaturated fatty acids (Dunstan et al. 2003, J Allergy Clin Immunol 112: 1178-1184) have been documented. Dietary polyphenols and polyphenol rich plant materials have also been studied extensively in numerous disease models and published data suggest that their presence may have an important role in preventing tissue damage due to oxidative stress and hence might have an anti-allergic potential.

For example, Zurcher et al., 2010, Clinic Exp Allergy, 40(6): 942-50, disclose that polyphenol-enriched apple extract attenuates food allergy in mice. Thereby, consumption of an apple extract particularly rich in flavonols reduced the symptoms of food allergy upon challenge. Lee et al., 2010, Inflamm Res 59:847-854, disclose that specifically the flavonols quercetin and kaempferol suppress IgE mediated allergic inflammation in an in vitro system. Tea extracts have been studied for their efficacy in skin inflammation in animal models (Camouse et al., 2009, Exp Dermatol 18: 522-526). Further, Oolong tea, a traditional Chinese tea, is reported to have anti-allergic activities (Ohmori et al. 1995, Biol Pharm Bull 18: 683-686). Tea extracts are particularly rich in flavanols such as catechins, epicatechins and their derivatives. Epi-gallocatechin gallate (EPCG) was found to be the active ingredient in tea extracts that provide protection against cutaneous inflammation (Katiyar et al. 1995, Photochem Photobiol 62: 855-861).

The effect of polyphenols has also been investigated for respiratory allergies. Nauta et al., 2008, Eur J Pharmacol 585: 354-360) disclose the in vitro effect of green tea and some isolated polyphenols on allergic effector cells such as mast cells and basophils. Thereby, EGCG was identified as the effective inhibiting agent.

Usually, natural extracts of plant materials such as from apple or tea contain only small amounts of those active ingredients identified so far. This may make it difficult to practically apply those extracts to patients in need for example, of an effective daily dose.

Further, the choice of natural compounds isolated from food grade materials which demonstrate a potential for preventing or reducing allergic symptoms is still very limited. It would be an advantage to know more such compounds in order to compare and assess their individual activities, to optimize and strengthen the effects of compositions comprising such active compounds, and to ultimately provide solutions which can be part of a natural daily diet to patients in need.

There still remains a need to find new and alternative compounds to prevent and reduce the symptoms of an allergic disorder or allergic reaction, without some of the inconveniences as mentioned above and/or for complementing the already existing choice of active ingredients. Particularly, the new solution should not have adverse health or side-effects upon a prolonged consumption, and the compound should ideally be available from a natural source and in amounts, which would make it practical and feasible to be consumed by an individual for example as part of a daily diet in a high enough dose for being effective.

SUMMARY OF THE INVENTION

The object of the present invention is to improve the state of the art and to provide a new and alternative solution for preventing and/or reducing the symptoms of an allergic disorder or allergic reaction.

The object of the present invention is achieved by the subject matter of the independent claims. The dependent claims further develop the idea of the present invention.

Accordingly, the present invention provides in a first aspect epicatechin for use in the prevention or reduction of symptoms of an allergic disorder and/or an allergic reaction.

Thereby, symptoms of an allergic disorder and/or allergic reaction pertain to the "secondary prevention of allergies" (Prevention of Allergy and Allergic Asthma, World Health Organization, 2003; WHO/NMH/MNC/CRA/03.2.).

It is one advantage of the present invention that it allows treating or preventing symptoms of an allergic disorder and/or an allergic reaction early, i.e. in the framework of a secondary prevention, while many existing therapies only allow a tertiary prevention.

The WHO discriminates between primary, secondary and tertiary prevention.

Primary Prevention is the prevention of immunological sensitization (i.e, the development of IgE antibodies).

Secondary Prevention is preventing the development of an allergic disease following sensitization and especially development of atopic eczema/atopic dermatitis, upper respiratory allergy, and allergic asthma.

Tertiary Prevention is the treatment of asthma and allergic diseases.

"Secondary prevention of allergies" is the effect of modulating the symptoms of allergies, i.e. the occurrence or intensity of the allergic reaction in a patient already sensitized to one or several allergens when the patient is re-exposed to said allergen(s). By modulating the occurrence or intensity of the allergic symptom(s), the inconvenience associated with allergies is minimized.

Polyphenols are a large group of small compounds with anti-oxidant activity that are commonly found in plants and fruits. Flavonoids are a sub-group of such polyphenols with shared structural features that themselves can be further sub-grouped for examples into flavonols, flavanols, flavones, flavanones and others. Compounds contained in apples and in green tea, for example, have been demonstrated to have a general effect on allergies. Apples are rich in various polyphenols, including quercetin and phlorizidin; green tea is rich in different flavanols including procyanidins and gallated derivatives of catechins and epicatechins. Thereby, it has been discovered that particularly quercetin and epigallocatechin gallate (EGCG) are the active ingredients which provide protection against inflammation and against allergies. It has now been surprisingly found by the inventors that the flavanol epicatechin is capable of reducing or preventing symptoms of an allergic disorder and/or allergic reaction. Evidence therefore performed in in vivo studies with mice is provided in the example section below.

Advantageously now, plant or fruit extracts rich in epicatechin or extracts supplemented with epicatechin or epicatechin in isolated or synthesized form per se, can be used in the prevention or reduction of symptoms of an allergic disorder or an allergic reaction. No undesired side-effects e.g. resulting from a strong corticosteroid or anti-histaminic activity are expected from a moderate use of epicatechin. Furthermore, plant or fruit extracts can be prepared which are on one hand effective for reducing allergy symptoms and on the other hand still pleasant for consumption. It is now also possible to provide extracts with the appropriate concentration of the active ingredient epicatechin that can be consumed in reasonable and feasible amounts per day e.g. as part of a daily diet by a consumer.

DETAILED DESCRIPTION OF THE INVENTION

Figure 1:
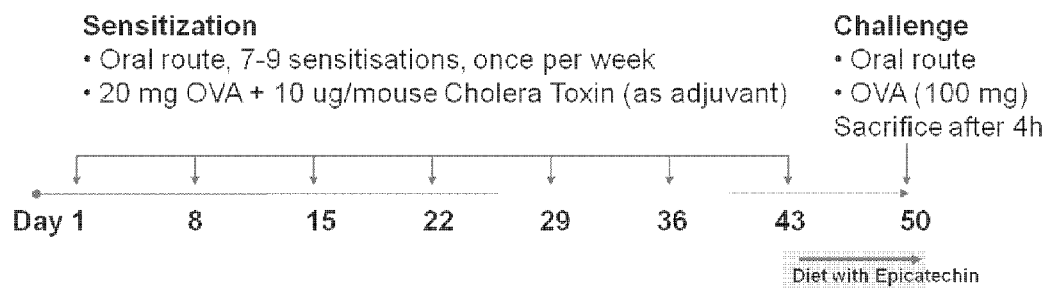
FIG. 1: Schematic presentation of the food allergy model used.

The present invention pertains to epicatechin for use in the prevention or reduction of symptoms of an allergic disorder and/or allergic reaction, wherein the allergic disorder is selected from the group consisting of skin allergy, allergic contact dermatitis, food allergy, allergic rhinitis or asthma.

Allergies may start especially in predisposed individuals from early infancy on, i.e. as skin allergy, for example as atopic eczema, limited to or followed by the development of food allergies, e.g. against certain cow's milk proteins, eggs and wheat proteins, nuts or shell fish. Respiratory allergies, for example allergic rhinitis and allergic asthma, occur later in life. Allergies represent a dysregulated immune response to a variety of allergens normally present either in the environment, e.g. dust mite, plant pollen, or in foods, e.g. milk, eggs, nuts.

The term "skin allergy" refers herein to itchy skin and rashes. One form of skin allergy typically is atopic dermatitis (eczema) which frequently occurs in young children. It may also start in young adults, and can continue into adult life. Further included under skin allergy is urticaria, also commonly called hives, which is an itchy rash that can occur at any age.

The term "allergic contact dermatitis" refers herein to contact dermatitis, which is caused from skin contact with a substance that causes a rash-like reaction. People react to a variety of chemicals, including cosmetics, hair dye, metals, topical medications, dental materials and plants, for example of the Toxicodendron family. Such contact allergies occur at all ages of a person or animal.

The term "food allergy" refers herein to an adverse immune response to a food, particularly a food protein. The most common foods known that trigger allergy reactions are milk, egg, peanuts, tree nuts, fish, shellfish, soy, and wheat. Some of these food allergens may become outgrown with age, but some such as peanut and shellfish, may remain a lifelong allergy for a subject. The symptoms of food allergy can range from a localized immune reaction e.g. eosinophilic esophagitis or be manifested systemically as cyanosis, diarrhea, hypothermia and anaphylaxis.

The term "allergic rhinitis", also commonly known as pollenosis or hay fever, refers herein to an allergic inflammation of the nasal airways and characterized by blocked and runny nose, sneezing and itching. Ocular symptoms such as red and watery eyes can also manifest. It occurs when an allergen, such as pollen or dust mite, is inhaled by an individual with a sensitized immune system. In such individuals, the allergen triggers the production of the antibody immunoglobulin E (IgE).

The term "asthma" refers herein to the common chronic inflammatory disease of the lower airways and characterized by wheezing, mucus production and impaired lung function.

The epicatechin is for use according to the invention, wherein the symptoms may be gut discomfort, diarrhea, vomiting, skin irritation, atopic eczema, respiratory irritation, ocular irritation, or a combination thereof.

The effect of the epicatechin is more specifically an effect on the secondary prevention of allergies. The symptoms of allergies, in the mouse model of the examples described below, are indeed reduced significantly as illustrated by lower allergic clinical scores. Generally, the symptoms can include all or a selection of the usually recognized symptoms of allergies. Such symptoms include cutaneous (redness of skin, rash, itchiness, dermatitis, eczema), ocular (itching and watering of the eyes), gastrointestinal (congestion, abdominal pain, cramps, vomiting, diarrhea), respiratory (itching of the nose, sneezing, nasal congestion, rhinitis, asthma) and in severe cases systemic (dizziness, mental confusion, immobility, anaphylaxis) manifestations.

The inventors have evidenced that allergic reactions and symptoms can be alleviated when sensitized young mammals are provided with an extract rich in epicatechin or with epicatechin in isolated form. The animal model mimics food allergy in humans, when humans, typically infants or young children, are naturally sensitized to food allergens. This defines the positive effect of epicatechin on the secondary prevention of allergies.

Hence, in a preferred embodiment of the present invention the allergic disorder and/or allergic reaction may be a food allergy.

The epicatechin is to be administered to a human being or a pet animal, in particular a cat or a dog.

The epicatechin can be administered to a human being at all ages. However, advantageously, administration of epicatechin to a patient starts as soon as an allergy and its symptoms starts to manifest, i.e. in many instances already early in life. Hence, preferably, the human being is a young child between the age of 4 months and six years or an older child up to the age of 18 years or an adult person.

In an alternative embodiment, the epicatechin is intended for consumption by an animal, preferably a cat or a dog. Similarly as with humans, allergies and symptoms of such allergies can be observed with animals, in particular with domesticated animals and animals kept as pets. Advantageously, the current invention provides a solution which can be provided to a companion animal by his owner.

The epicatechin is administered to a human being in an amount in the range from 25 mg to 10 g per day, from 50 mg to 10 g per day, preferably from 100 mg to 5 g per day, even more preferably from 300 mg to 1 g per day. These preferred doses allow to provide on one hand sufficient epicatechin to a relevant patient per day in order to provide the expected health benefit and on the other hand not to overdose epicatechin to prevent the risk of any potential undesirable or toxic effects to the patient.

In one of the embodiments, the epicatechin is provided in the form of a plant extract or concentrate. This allows providing the epicatechin in its natural form and environment, but in concentrated condition. Thereby, the epicatechin is of natural origin and can be provided in a food product which is well recognized and appreciated by a consumer and still provide him with the necessary amount of active epicatechin. A further advantage is that the epicatechin does not need to be first produced in purified form, e.g. via chemical synthesis, and hence provides also a more economic solution for providing the epicatechin to a consumer.

Advantageously, the epicatechin is provided in the form of a plant extract which naturally already contains substantial levels of epicatechin and which are well liked by the consumers. Thereby, the plant extract or concentrate can preferably be an extract or concentrate from apple, cocoa or tea.

In a preferred embodiment, the epicatechin is provided in the form of a composition comprising at least 0.1 wt %, preferably at least 1 wt % epicatechin. Alternatively, the epicatechin is provided in the form of a composition comprising at least 10 wt %, for example at least 20 wt % or 40 wt %. Thereby, the composition can be enriched with epicatechin either by concentrating the already naturally present epicatechin therein, or supplementing the composition with for example a plant extract rich in epicatechin or with synthetically produced epicatechin. Advantageously, the resulting composition comprises epicatechin in such an amount that it is effective upon a normal, feasible daily consumption of said composition, for example if part of a food product. Thereby, for example a composition comprising 0.1 to 1 wt % epicatechin may be well adapted for a composition provided to a young child as part of a regular meal. Alternatively, an adult person may prefer a more epicatechin concentrated composition which may be consumed between meals and not as part of a regular meal.

The epicatechin for use of the invention is provided in the form of a composition, which is a food product, a food supplement or a pharmaceutical product.

In a preferred embodiment, the food product is selected from the group consisting of an infant feeding composition, a follow-up formula, a growing-up milk, an infant cereal, or a baby food product. These products are particularly well suited to address and solve the problem of the prevention or reduction of symptoms of allergies in babies and young children.

In a further embodiment, the food product is selected from the group consisting of a beverage product, a yoghurt product, a fermented milk, a fruit juice, or a cereal bar. These food products are well suited for administering epicatechins to older children and adult humans. The food products can well be enriched with epicatechin and have a credible image to provide a health oriented functional food product to the consumers.

A particular need for products to reduce symptoms of allergies may be in the clinical environment, such as in hospitals, clinics and homes for elderly persons. Therefore, in a still further embodiment, the food product is a food for specific medical purposes such as a health care food product for oral feeding, and/or a nutritional product for enteral feeding. The advantage of the invention is that the active ingredient epicatechin can be provided in relatively high local concentration and low volumes of a medical food product and hence be administered effectively to patients in such need.

In a still further embodiment, the food product is a pet food product.

Those skilled in the art will understand that they can freely combine all features of the present invention disclosed herein. In particular, features described for different embodiments of the present invention may be combined. Further advantages and features of the present invention are apparent from the figures and examples.

Example 1: Ovalbumin (OVA) Food Allergy Mouse Model

As schematically shown in FIG. 1, six weeks old conventional BALB/c mice were sensitized by the oral route (with a gavage needle)—3 applications in the first week and then at weekly intervals with 20 mg of Ovalbumin (OVA) from Sigma (Switzerland) plus 10 µg/mouse of Cholera toxin (used as adjuvant) from LuBioscience (Lucerne, Switzerland) during 7 weeks. Epicatechin as pure isolated polyphenol or enriched in a plant or fruit extract at a dose ranging from 0.1% to 1% was incorporated into the food and given to sensitized mice during the last week of the experiments. One week after the last sensitization, an oral challenge via gavage with 100 mg of OVA was performed. On the day of the challenge, mice were starved for 2 hours before challenge. Thirty minutes after the challenge, the mice were individually observed during 30 min. Clinical symptoms were recorded and quantified as follows (Allergic Score): 0) no symptoms, less than 4 episodes of scratching; 1) 4-10 episodes of scratching around the nose and head, no diarrhoea; 2) more than 10 episodes of scratching or soft stool; 3) diarrhoea or laboured respiration or cyanosis or the presence of two or more symptoms (scratching and soft stool); 4) diarrhoea in combination with immobility after prodding, bristled fur, laboured respiration or cyanosis; 5) anaphylaxis. Four hours after the challenge, the mice were sacrificed.

Figure 2:
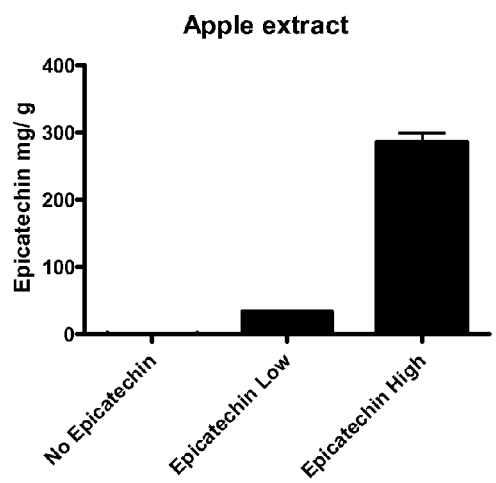
FIG. 2: Concentration of epicatechin in the different studied apple extracts.
Figure 3:
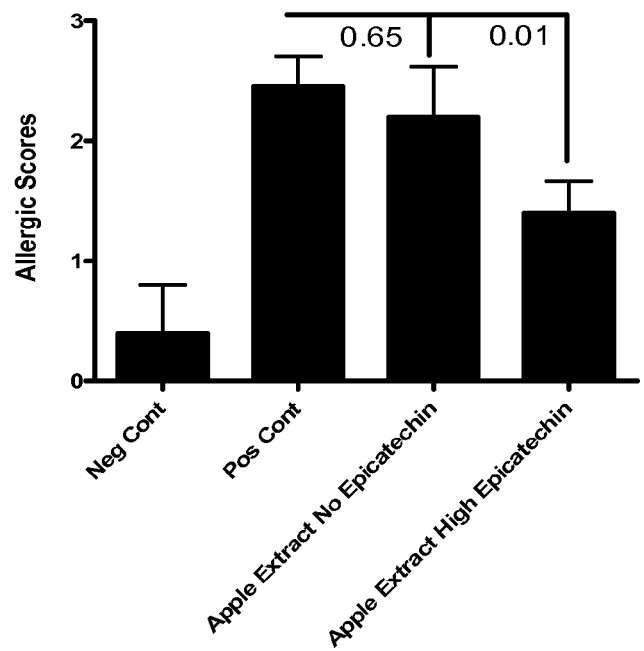
FIG. 3: Result of the allergy symptoms test with mice treated with apple extracts with and without high concentration of epicatechin.

Example 2: Allergy Symptoms Test with Apple Extracts with and without High Levels of Epicatechin Apple extracts with different concentrations of epicatechin (FIG. 2) were included as 1 wt % into the diet (Kliba 3200, Kliba Nafag Kaiseraugst, Switzerland) of the sensitized mice during the last week of the experiments. The diet was provided starting at the end of the sensitization phase and the mice received the apple extract containing diet for a total duration of 8 days. After the challenge at day 50, the mice that were treated with the epicatechin containing apple extracts developed less severe clinical symptoms than the control sensitized, untreated animals (the positive controls). However, the sensitized mice that received apple extract containing no epicatechin had no relief in allergic symptoms. The results are illustrated in FIG. 3.

Example 3: Allergy Symptoms Test with Cocoa Exact Rich in Epicatechin

Figure 4:
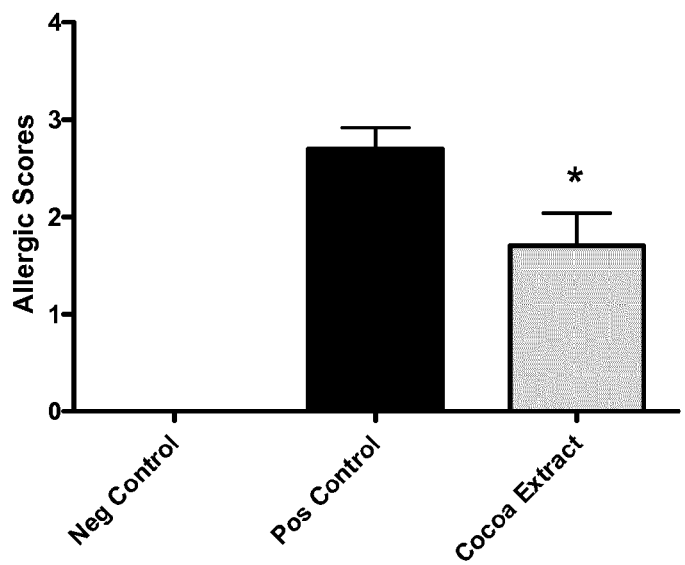
FIG. 4: Result of the allergy symptoms test with mice treated with cocoa exact rich in epicatechin.

Cocoa extract enriched in epicatechin was administered in 1 wt % concentration in the diet to sensitized mice during the last week of the allergy symptoms model experiment in the same way as the apple extracts in Example 2. After the challenge at day 50, mice that were treated with the epicatechin containing cocoa extract developed significantly less severe clinical allergy symptoms than the control sensitized, untreated animals (the positive controls). The results are illustrated in FIG. 4.

Figure 5:
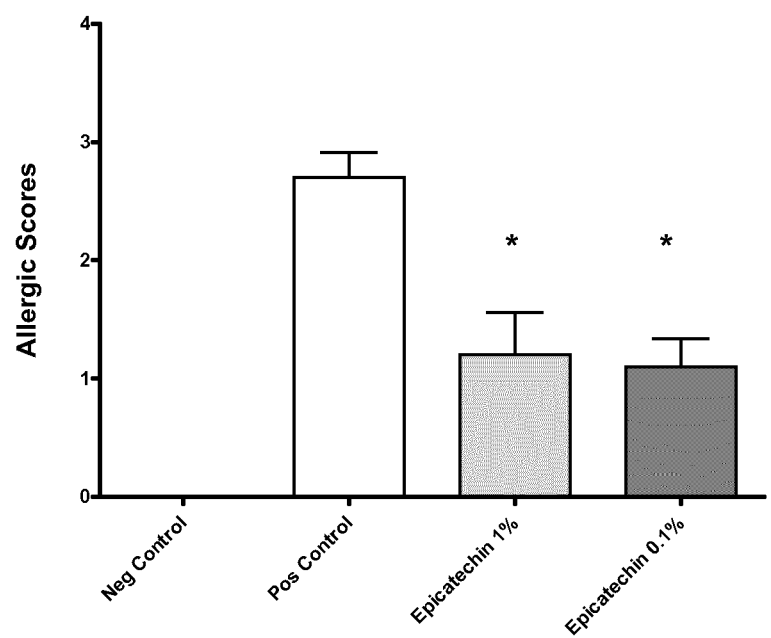
FIG. 5: Result of the allergy symptoms test with mice treated with chemically pure epicatechin.

Example 4: Allergy Symptoms Test with Pure Epicatechin at Different Concentrations Chemically pure epicatechin (Sigma, Switzerland) was administered in the diet in a dose ranging from 0.1 to 1 wt % to sensitized mice during the last week of the allergy symptoms model in the same way as the apple extracts in Example 2. After the challenge at day 50, the mice treated with the polyphenol epicatechin at both 0.1% and 1% concentrations in the diet, developed significantly less severe clinical allergy symptoms than the sensitized, untreated animals (the positive controls). The results are illustrated in FIG. 5.

The invention claimed is:

1. A method for the secondary prevention of an allergic disorder and/or an allergic reaction in a patient in need of same comprising administering a composition comprising at least 0.1 wt. % epicatechin.

2. The method according to claim 1, wherein the allergic disorder is selected from the group consisting of skin allergy, allergic contact dermatitis, food allergy, allergic rhinitis and asthma.

3. The method according to claim 1, wherein the secondary prevention is treating or preventing symptoms of an allergic disorder and/or an allergic reaction, wherein the symptoms are selected from the group consisting of gut discomfort, diarrhea, vomiting, skin irritation, atopic eczema, respiratory irritation, ocular irritation, and a combination thereof.

4. The method according to claim 1, wherein the patient is a human being or a pet animal.

5. The method according to claim 1, wherein the patient is selected from the group consisting of a young child between the age of 4 months and six years, an older child between the age of 6 to 18 years, and an adult person.

6. The method according to claim 1, wherein the epicatechin is administered in an amount in the range from 25 mg to 10 g per day.

7. The method according to claim 1, wherein the epicatechin is provided in the form of a plant extract or concentrate.

8. The method according to claim 7, wherein the plant extract or concentrate is an extract or concentrate from a plant selected from the group consisting of apple, cocoa and tea.

9. The method according to claim 1, wherein the epicatechin comprises at least 10 wt % of the composition.

10. The method according to claim 1, wherein the composition is selected from the group consisting of a food product, a food supplement and a pharmaceutical product.

11. The method according to claim 10, wherein the food product is selected from the group consisting of an infant feeding composition, a follow-up formula, a growing-up milk, an infant cereal, and a baby food product.

12. The method according to claim 10, wherein the food product is selected from the group consisting of a beverage product, a yoghurt product, a fermented milk, a fruit juice, and a cereal bar.

13. The method according to claim 10, wherein the food product is a food for specific medical purposes.

14. The method according to claim 10, wherein the food product is a pet food product.

15. The method according to claim 1, wherein epicatechin is the only polyphenol in the composition.

* * * * *